(12) United States Patent
Suzuki et al.

(10) Patent No.: US 8,455,674 B2
(45) Date of Patent: Jun. 4, 2013

(54) CHLOROTHIOFORMATE MANUFACTURING METHOD

(75) Inventors: Toshiaki Suzuki, Niihama (JP); Fumi Yonehara, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/140,361

(22) PCT Filed: Dec. 18, 2009

(86) PCT No.: PCT/JP2009/071101
§ 371 (c)(1),
(2), (4) Date: Jun. 16, 2011

(87) PCT Pub. No.: WO2010/071192
PCT Pub. Date: Jun. 24, 2010

(65) Prior Publication Data
US 2011/0251429 A1    Oct. 13, 2011

(30) Foreign Application Priority Data

Dec. 19, 2008 (JP) .................................. 2008-323470

(51) Int. Cl.
*C07C 329/06* (2006.01)
*C07C 51/58* (2006.01)

(52) U.S. Cl.
CPC .................................. *C07C 329/06* (2013.01)

USPC .......................................... 558/249; 562/856

(58) Field of Classification Search
CPC ...................................................... C07C 329/06
See application file for complete search history.

(56) References Cited

U.S. PATENT DOCUMENTS 4,340,746 A * 7/1982 Semler et al. ................... 549/78

FOREIGN PATENT DOCUMENTS

| HU | 202488 B | | 3/1991 |
|---|---|---|---|
| JP | 56-034663 A | | 4/1981 |
| JP | 2007-204428 A | * | 8/2007 |
| JP | 2007-204428 A | | 8/2007 |
| JP | 2007-290987 A | | 11/2007 |

OTHER PUBLICATIONS

Chinese Office Action issued in Chinese Application No. 2009801498685, dated Mar. 28, 2013.

* cited by examiner

*Primary Examiner* — Paul A Zucker
(74) *Attorney, Agent, or Firm* — Sughrue Mion, PLLC

(57) ABSTRACT

The present invention relates to a process for producing chlorothioformate comprising reacting an alkenyl mercaptan with phosgene in a reactor in the presence of a carboxylic acid amide in an organic solvent, characterized in that the carboxylic acid amide is preliminary charged to the reactor in an amount of 10 to 50% by weight based on the whole amount of the carboxylic acid amide, and subsequently, the compound of the formula (I), phosgene and the remaining carboxylic acid amide are charged to the reactor.

5 Claims, No Drawings

CHLOROTHIOFORMATE MANUFACTURING METHOD

CROSS REFERENCE TO RELATED APPLICATIONS

This application is a National Stage of International Application No. PCT/JP2009/071101, filed Dec. 18, 2009, which claims priority from Japanese Patent Application No. 2008-323470, filed Dec. 19, 2008, the contents of all of which are incorporated herein by reference in their entirety.

FIELD OF THE INVENTION

The present invention relates to a process for producing a compound of the formula (II):

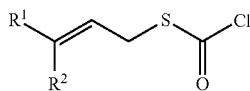

wherein $R^1$ and $R^2$ independently of one another represent a hydrogen atom or a $C_{1-4}$ alkyl group,
by reacting a compound of the formula (I):

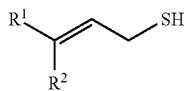

wherein $R^1$ and $R^2$ independently of one another represent the same meaning as described above,
with phosgene in a reactor in the presence of a base catalyst in an organic solvent.

Hereinafter, the compound of the formula (I) and the compound of the formula (II) will be also referred to as the alkenyl mercaptan (I) and the chlorothioformate (II), respectively.

BACKGROUND ART

JP-A-2007-204428 discloses a process for producing the chlorothioformate (II) by reacting the alkenyl mercaptan (I) with phosgene in a reactor in the presence of a base catalyst in an organic solvent, in which a carboxylic acid amide is used in an amount of 0.05 mole per mole of the alkenyl mercaptan (I) and the alkenyl mercaptan (I), phosgene and the carboxylic acid amide are charged to the reactor containing no carboxylic acid amide, or alternatively, a carboxylic acid amide is used in an amount of 0.05 mole per mole of the alkenyl mercaptan (I) and phosgene is charged to the reactor to which the whole amount of the alkenyl mercaptan (I) and the whole amount of the carboxylic acid amide are already charged.

JP-A-2007-290987 discloses a process for producing the chlorothioformate (II) by reacting the alkenyl mercaptan (I) with phosgene in a reactor in the presence of a secondary or tertiary amine catalyst in an organic solvent, in which triethylamine is used in an amount of 0.05 mole per mole of the alkenyl mercaptan (I) and the alkenyl mercaptan (I) and triethylamine are preliminarily charged to the reactor in an amount of 25% by weight based on the whole amount of the alkenyl mercaptan (I) and the amount of 25% by weight based on the whole amount of triethylamine, respectively and subsequently, the remaining alkenyl mercaptan (I), phosgene and the remaining triethylamine are charged to the reactor, or alternatively, triethylamine is used in an amount of 0.05 mole per mole of the alkenyl mercaptan (I) and phosgene is charged to the reactor to which the whole amount of the alkenyl mercaptan (I) and the whole amount of triethylamine are already charged.

SUMMARY OF THE INVENTION

However, the amount of a compound of the formula (III):

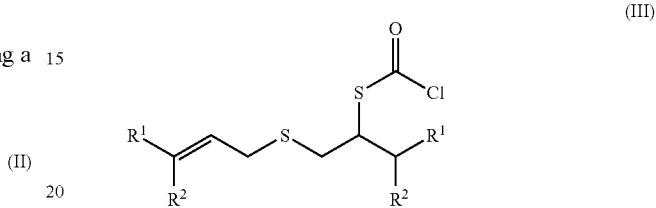

wherein $R^1$ and $R^2$ independently of one another represent the same meaning as described above,
which is produced as a by-product besides the chlorothioformate (II) targeted, may increase in the above-mentioned processes. Accordingly, the above-mentioned processes are not necessarily satisfactory in the quality and the yield of the chlorothioformate (II).

Hereinafter, the compound of the formula (III) will be also referred to as the by-product (III).

An object of the present invention is to provide a process for producing the chlorothioformate (II) which can suppress the formation of the by-product (III) and produce the high quality chlorothioformate (II) in a good yield.

The present invention provides a process for producing a compound of the formula (II):

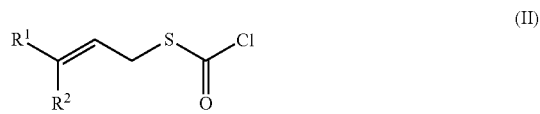

wherein $R^1$ and $R^2$ independently of one another represent a hydrogen atom or a $C_{1-4}$ alkyl group,
comprising reacting a compound of the formula (I):

wherein $R^1$ and $R^2$ independently of one another represent the same meaning as described above,
with phosgene in a reactor in the presence of a carboxylic acid amide in an organic solvent,
wherein the carboxylic acid amide is preliminary charged to the reactor in an amount of 10 to 50% by weight based on the whole amount of the carboxylic acid amide, and subsequently, the compound of the formula (I), phosgene and the remaining carboxylic acid amide, i.e., 50 to 90% by weight based on the whole amount of the carboxylic acid amide, are charged to the reactor.

EFFECTS OF THE INVENTION

According to the present invention, the formation of the by-product (III) can be sufficiently suppressed and the high quality chlorothioformate (II) can be produced in a good yield.

EMBODIMENTS OF THE INVENTION

In the production process of the present invention, the alkenyl mercaptan (I) is reacted with phosgene. In the formula (I), examples of the $C_{1-4}$ alkyl groups include a methyl group, an ethyl group, a n-propyl group, an isopropyl group, a n-butyl group, a sec-butyl group and a ter-butyl group. Examples of the alkenyl mercaptan (I) include 2-propenyl mercaptan (allyl mercaptan), 2-butenyl mercaptan, 3-methyl-2-butenyl mercaptan, 2-pentenyl mercaptan, 2-hexenyl mercaptan, 2-heptenyl mercaptan and the like. Preference is given to the use of 2-propenyl mercaptan (allyl mercaptan).

Phosgene is usually used in an amount of 1 mole or more, preferably from 1.05 to 2 moles, per mole of the alkenyl mercaptan (I). Phosgene may be used in the form of gas or liquid.

In the production process of the present invention, the reaction can smoothly proceed since a carboxylic acid amide is used as a catalyst. The carboxylic acid amide may be N,N-disubstituted carboxylic acid amide, N-monosubstituted carboxylic acid amide or unsubstituted carboxylic acid amide. The typical example is a compound of the formula (IV):

$$R^3\text{---}C(=O)\text{---}NR^4R^5 \qquad (IV)$$

wherein $R^3$, $R^4$ and $R^5$ independently of one another represent a hydrogen atom, an alkyl group or an aryl group.

Examples of the alkyl groups include a methyl group, an ethyl group, a propyl group, a butyl group and the like. In addition, Examples of the aryl groups include phenyl group, naphthyl group and the like. Preference is given to the use of N,N-dialkyl carboxylic acid amide of the formula (IV) in which both $R^4$ and $R^5$ are alkyl groups, in particular, lower alkyl groups such as $C_{1-5}$ alkyl groups.

The carboxylic acid amide is usually used in an amount of 0.01 to 0.09 mole per mole of the alkenyl mercaptan (I). When the carboxylic acid amide is used in an amount of 0.01 mole or more per mole of the alkenyl mercaptan (I), the reaction may smoothly proceed. When the carboxylic acid amide is used in an amount of from 0.09 mole or less per mole of the alkenyl mercaptan (I), the amount of the by-product (III) produced may decrease.

As an organic solvent, a water-immiscible solvent is preferably used since a mixture of a reaction solution and water for oil and water is easily separated to an oil phase and an aqueous phase in a post-treatment after the reaction. Examples include aliphatic hydrocarbons such as hexane, heptane and octane; alicyclic hydrocarbons such as cyclopentane and cyclohexane; aromatic hydrocarbons such as benzene, toluene and xylene; halogenated aliphatic hydrocarbons such as dichloromethane, chloroform and 1,2-dichloroethane; halogenated aromatic hydrocarbons such as monochlorobenzene and dichlorobenzene; ethers such as diethyl ether and dibutyl ether; esters such as ethyl acetate and butyl acetate, and the like. An aromatic hydrocarbon is preferably used.

The organic solvent is usually used in an amount of 1 to 10 parts by weight, preferably 1 to 5 parts by weight, per part by weight of the alkenyl mercaptan (I).

In the production process of present invention, the carboxylic acid amide is preliminarily charged to a reactor in an amount of 10 to 50% by weight based on the whole amount of the carboxylic acid amide, and subsequently, the alkenyl mercaptan (I), phosgene and the remaining carboxylic acid amide, i.e., 50 to 90% by weight based on the whole amount of the carboxylic acid amide, are charged to the reactor. In this way, the formation of the by-product (III) of the formula (III) can be sufficiently suppressed and the high quality chlorothioformate (II) can be produced in a good yield. Preferably, the amount of the carboxylic acid amide which is preliminarily charged to a reactor is 30 to 50% by weight based on the whole amount of the carboxylic acid amide.

The whole amount of the alkenyl mercaptan (I) may be charged to a reactor together with phosgene and the given amount of the carboxylic acid amide. Alternatively, a part of the alkenyl mercaptan (I) may be preliminarily charged to a reactor, and subsequently, the remaining alkenyl mercaptan (I) may be charged to the reactor together with phosgene and the given amount of the carboxylic acid amide.

Likewise, the whole amount of phosgene may be charged to a reactor together with the alkenyl mercaptan (I) and the given amount of the carboxylic acid amide. Alternatively, a part of phosgene may be preliminarily charged to a reactor, and subsequently, the remaining phosgene may be charged to the reactor together with the alkenyl mercaptan (I) and the given amount of the carboxylic acid amide.

An organic solvent may be preliminarily charged to a reactor. Alternatively, the organic solvent may be charged to a reactor together with the alkenyl mercaptan (I), phosgene and the carboxylic acid amide.

The alkenyl mercaptan (I) and phosgene may be continuously supplied without interval or discontinuously supplied. The supply of the alkenyl mercaptan (I) and phosgene may not necessarily started at the same time and may be started at the staggered times as far as the effect of the present invention is achieved. In addition, the supply of the alkenyl mercaptan (I) and phosgene may not be necessarily finished at the same time and may be finished at staggered times as far as the effects of the present invention are achieved. In general, the amount of the alkenyl mercaptan (I) supplied together with phosgene may be 80% by weight or more based on the whole amount of the alkenyl mercaptan (I) used. Also, the amount of phosgene supplied together with the alkenyl mercaptan (I) may be 80% by weight or more based on the whole amount of phosgene used.

Preferably, the alkenyl mercaptan (I) is supplied after cooling. As a result, the formation of the by-product (III) may be suppressed. In addition, the formation of a disulfide by the oxidation of two molecules of the alkenyl mercaptan (I) and the formation of a thiol carbonate by the reaction of the alkenyl mercaptan (I) with chlorothioformate may be suppressed. A temperature for cooling the alkenyl mercaptan (I) depends on the kind of the alkenyl mercaptan (I). Usually, the cooling temperature is typically from −20 to 5° C.

The reaction temperature is usually from 0 to 80° C., preferably from 30 to 50° C. In addition, the reaction is usually carried out around atmospheric pressure. However, the reaction may be optionally carried out under increased pressure or decreased pressure. The reaction can be carried out continuously, semicontinuously or batchwise.

The reaction mixture containing the chlorothioformate of the formula (II) with high quality can be obtained in a good yield. A method of a post-treatment after the reaction may be suitably selected. Preferably, water, preferably acidic water is added to the reaction mixture to hydrolyze excessive phosgene which may remain in the reaction mixture, and then the mixture is separated into an oil phase and a aqueous phase to obtain a solution of chlorothioformate in an organic solvent as the organic phase. The solution obtained may be optionally refined by washing, distillation, crystallization or the like, and used for the various applications.

EXAMPLES

The Examples of the present invention will be shown below. However, the present invention is not limited thereto. In the Examples, the yield and the content of allyl chlorothioformate (a compound of the formula (II) in which $R^1$ and $R^2$ are hydrogen atoms) were determined by gas chromatography analysis. The content of the by-product (III) (a compound of the formula (III) in which $R^1$ and $R^2$ are hydrogen atoms) were calculated from an area ratio of the amide compound of the by-product (III) to the amide compound of the chlorothioformate (II), which was determined by gas chromatography analysis of a solution prepared by adding an amine to a reaction mixture sampled after the reaction.

Reference Example 1

Preparation of Allyl Mercaptan (a Compound of the Formula (I) in which $R^1$ and $R^2$ are Hydrogen Atoms)

230.30 g (2.868 moles) of sodium hydrosulfide hydrate (a content of sodium hydrosulfide =70% by weight, a content of sodium sulfide =4.20% by weight, a content of sodium hydrosulfide in sodium sulfide =6.0% by weight), 200.11 g of water, 160.02 g of xylene, 111.24 g (0.333 mole) of a 69.6% by weight aqueous solution of benzyltriethylammonium chloride were charged to a glass reactor equipped with a reflux condenser, a thermometer, a stirrer and a jacketed dropping funnel, and stirred. Nitrogen was introduced into the gaseous phase in the reactor to maintain a nitrogen atmosphere.

Subsequently, 200.01 g (2.561 moles) of allyl chloride was charged to the jacketed dropping funnel and cooled to −2 to 5° C. Allyl chloride cooled was dropwise added over 7 hours while maintaining a reaction solution at 40° C. and the reaction solution was further maintained at 40° C. for 3 hours. The reaction solution obtained was cooled to 0° C. to 10° C. Then, 240.11 g of water was added to the reaction solution to dissolve sodium chloride precipitated. Then, the reaction solution was separated to an oil phase and an aqueous phase to obtain 345.67 g of a solution of allyl mercaptan in xylene as an organic phase. The xylene solution was analyzed by gas chromatography. The yield of allyl mercaptan based on allyl chloride was 83.92%.

Example 1

65.34 g (0.402 mole) of allyl mercaptan obtained by the process described in Reference Example 1, 2.37 g (0.032 mole, 40% by weight based on the whole amount of N,Ndimethylformamide) of N,N-dimethylformamide and 403.21 g of xylene were charged to a glass reactor equipped with a phosgene gas inlet, a reflux condenser, a thermometer, a stirrer and a jacketed dropping funnel and stirred. Subsequently, nitrogen was introduced into the gaseous phase in the reactor to maintain a nitrogen atmosphere. Then, 41.80 g (0.423 mole) of phosgene was introduced into the reaction solution over 2 hours while maintaining the reaction solution at a temperature of 39 to 41° C. Thereafter, a mixture of 195.31 g of allyl mercaptan (1.207 mole), 3.53 g (0.048 mole, 60% by weight based on the whole amount of N,N-dimethylformamide) of N,N-dimethylformamide was charged to the jacketed dropping funnel, cooled to 0 to 5° C. and dropwise added to the reaction solution over 5 hours while maintaining a temperature of the reaction solution at 39 to 41° C. Simultaneously, 104.50 g (1.056 moles) of phosgene was introduced into the reaction solution over 5 hours. Furthermore, 20.90 g (0.211 mole) of phosgene was introduced into the reaction solution over 1 hour while maintaining the reaction solution at a temperature of 39 to 41° C. Then, the reaction solution was maintained at a temperature of 39 to 41° C. for 3 hours. The reaction solution obtained was cooled to 0 to 5° C., and 264.08 g of water was added to the reaction solution to decompose the unreacted phosgene. The reaction solution was separated to an oil phase and an aqueous phase to obtain 740.76 g of xylene solution of allyl chlorothioformate as an organic phase.

The content of allyl chlorothioformate in the solution was 25.60% by weight. The yield of allyl chlorothioformate based on allyl mercaptan was 86.24%. As a result of gas chromatography analysis, the area ratio of the amide compound of the by-product (III) to the amide compound of the chlorothioformate (II) was 0.03%.

Comparative Example 1

80.00 g (0.521 mole) of allyl mercaptan obtained by the process described in Reference Example 1, 7.62 g (0.104 mole, 100% by weight based on the whole amount of N,N-dimethylformamide) of N,N-dimethylformamide and 496.00 g of xylene were charged to a glass reactor equipped with a phosgene gas inlet, a reflux condenser, a thermometer, a stirrer and a jacketed dropping funnel and stirred. Subsequently, nitrogen was introduced into the gaseous phase in the reactor to maintain a nitrogen atmosphere. Then, 51.54 g (0.521 mole) of phosgene was introduced into the reaction solution over 2 hours while maintaining the reaction solution at a temperature of 39 to 41° C. for 3 hours. Thereafter, 240.00 g (1.563 moles) of allyl mercaptan was put into the jacketed dropping funnel, cooled to 0 to 5° C. and dropwise added to the reaction solution over 6 hours while maintaining the reaction solution at a temperature of 39 to 41° C. Simultaneously, 154.61 g (1.563 moles) of phosgene was introduced into the reaction solution over 6 hours. Then, the reaction solution was maintained at the temperature of 39 to 41° C. for 3 hours. The reaction solution obtained was cooled to 0 to 5° C., and 379.91 g of 2% hydrochloric acid was added to the reaction solution to decompose the unreacted phosgene. Subsequently, the reaction solution was separated to an oil phase and an aqueous phase to obtain 910.60 g of xylene solution of allyl chlorothioformate as an organic phase.

The content of allyl chlorothioformate in the solution was 25.21% by weight. The yield of allyl chlorothioformate based on the allyl mercaptan was 80.64%. As a result of gas chromatography analysis, the area ratio of the amide compound of the by-product (III) to the amide compound of the chlorothioformate (II) was 0.17%.

Comparative Example 2

97.50 g (0.550 mole) of allyl mercaptan obtained by the process described in Reference Example 1, 17.68 g (0.242 mole, 11 mole % based on the whole amount of allyl mercaptan, 100% by weight based on the whole amount of N,N-dimethylformamide) of N,N-dimethylformamide and 604.50 g of xylene were charged to a glass reactor equipped with a phosgene gas inlet, a reflux condenser, a thermometer, a stirrer and a jacketed dropping funnel and stirred. Nitrogen was introduced into the gaseous phase in the reactor to maintain a nitrogen atmosphere. Then, 54.37 g (0.550 mole) of phosgene was introduced into the reaction solution over 2 hours while maintaining the reaction solution at a temperature of 39 to 41° C. Thereafter, 292.50 g (1.649 moles) of allyl mercaptan was charged to the jacketed dropping funnel, cooled to 0 to 5° C. and dropwise added to the reaction solution over 6 hours while maintaining the reaction solution at a temperature of 39 to 41° C. Simultaneously, 163.11 g (1.649 moles) of phosgene was introduced into the reaction solution over 6 hours. Then, the reaction solution was maintained at a temperature of 39 to 41° C. for 3 hours. The reaction solution obtained was cooled to 0 to 5° C., and 400.79 g of 2% hydrochloric acid was added to the reaction solution to decompose the unreacted phosgene. Then, the reaction solution was separated to an oil phase and an aqueous phase to obtain 1079.40 g of xylene solution of allyl chlorothioformate as an organic phase.

The content of allyl chlorothioformate in the solution was 21.59% by weight. The yield of allyl chlorothioformate based on allyl mercaptan was 77.60%. As a result of gas chromatography analysis, the area ratio of the amide compound of the by-product (III) to the amide compound of the chlorothioformate (II) was 0.72%.

Comparative Example 3

37.52 g (0.220 mole) of allyl mercaptan obtained by the process described in Reference Example 1, 1.78 g (0.018 mole, 40% by weight based on the whole amount of triethylamine) of triethylamine and 232.51 g of xylene were charged to a glass reactor equipped with a phosgene gas inlet, a reflux condenser, a thermometer, a stirrer and a jacketed dropping funnel and stirred. Nitrogen was introduced into the gaseous phase in the reactor to maintain a nitrogen atmosphere. Then, 22.83 g (0.231 mole) of phosgene was introduced into the reaction solution over 2 hours while maintaining the reaction solution at a temperature of 39 to 41° C. Thereafter, a mixture of 112.51 g (0.659 mole) of allyl mercaptan and 2.67 g (0.0264 mole, 60% by weight based on the whole amount of triethylamine) of triethylamine was charged to the jacketed dropping funnel, cooled to 0 to 5° C. and dropwise added to the reaction solution over 5 hours while maintaining the reaction solution at a temperature of 39 to 41° C. Simultaneously, 57.08 g (0.577 mole) of phosgene was introduced into the reaction solution over 5 hours. Moreover, 11.42 g (0.115 mole) of phosgene was introduced into the reaction solution over 1 hour while maintaining the reaction solution at a temperature of 39 to 41° C. Then, the reaction solution was maintained at a temperature of 39 to 41° C. for 3 hours. The reaction solution obtained was cooled to 0 to 5° C., and 143.29 g of water was added to the reaction solution to decompose the unreacted phosgene. Subsequently, the reaction solution was separated to an oil phase and an aqueous phase to obtain 416.11 g of xylene solution of allyl chlorothioformate as an organic phase.

The content of allyl chlorothioformate in the solution was 23.87% by weight. The yield of allyl chlorothioformate based on allyl mercaptan was 82.71%. As a result of the gas chromatography analysis, the area ratio of the amide compound of the by-product (III) to the amide compound of the chlorothioformate (II) was 0.05%.

The invention claimed is:

1. A process for producing a compound of the formula (II):

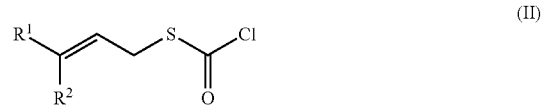

(II)

wherein $R^1$ and $R^2$ independently of one another represent a hydrogen atom or a $C_{1-4}$ alkyl group,
comprising reacting a compound of the formula (I):

(I)

wherein $R^1$ and $R^2$ independently of one another represent the same meaning as described above,
with phosgene in a reactor in the presence of a carboxylic acid amide in an organic solvent,
wherein the carboxylic acid amide is preliminary charged to the reactor in an amount of 10 to 50% by weight based on the whole amount of the carboxylic acid amide, and subsequently, the compound of the formula (I), phosgene and the remaining carboxylic acid amide are charged to the reactor.

2. The process according to claim 1, wherein the carboxylic acid amide is a N,N-dialkyl carboxylic acid amide.

3. The process according to claim 1, wherein the carboxylic acid amide is used in an amount of 0.01 to 0.09 mole per mole of the compound of the formula (I).

4. The process according to claim 1, wherein the compound of the formula (I) is allyl mercaptan.

5. The process according to claim 1, wherein the organic solvent is an aromatic hydrocarbon.

* * * * *